United States Patent
Sato et al.

(10) Patent No.: US 7,991,447 B2
(45) Date of Patent: Aug. 2, 2011

(54) BIOLOGICAL PHOTOMETRIC EQUIPMENT

(75) Inventors: Hiroki Sato, Fujimino (JP); Masashi Kiguchi, Kawagoe (JP); Atsushi Maki, Fuchu (JP); Tsuyoshi Yamamoto, Matsudo (JP)

(73) Assignees: Hitachi, Ltd., Tokyo (JP); Hitachi Medical Corporation, Tokyo (JP)

( * ) Notice: Subject to any disclaimer, the term of this patent is extended or adjusted under 35 U.S.C. 154(b) by 1490 days.

(21) Appl. No.: 10/577,944

(22) PCT Filed: Jul. 1, 2004

(86) PCT No.: PCT/JP2004/009678
§ 371 (c)(1),
(2), (4) Date: May 3, 2006

(87) PCT Pub. No.: WO2005/041771
PCT Pub. Date: May 12, 2005

(65) Prior Publication Data
US 2007/0135694 A1    Jun. 14, 2007

(30) Foreign Application Priority Data

Nov. 4, 2003    (JP) .................................. 2003-373891

(51) Int. Cl.
*A61B 5/1455* (2006.01)
(52) U.S. Cl. ................... 600/323; 600/310; 600/340
(58) Field of Classification Search ........... 600/300–350
See application file for complete search history.

(56) References Cited

U.S. PATENT DOCUMENTS

| | | | |
|---|---|---|---|
| 5,291,884 A * | 3/1994 | Heinemann et al. | 600/322 |
| 6,542,763 B1 * | 4/2003 | Yamashita et al. | 600/310 |
| 6,611,698 B1 | 8/2003 | Yamashita et al. | |
| 6,640,133 B2 | 10/2003 | Yamashita et al. | |

FOREIGN PATENT DOCUMENTS

| | | |
|---|---|---|
| EP | 0 271 340 | 6/1988 |
| EP | 1 327 418 | 7/2003 |
| JP | 09-098972 | 4/1997 |
| WO | WO 03/068070 | 8/2003 |

* cited by examiner

*Primary Examiner* — Eric F Winakur
*Assistant Examiner* — Marjan Fardanesh
(74) *Attorney, Agent, or Firm* — Antonelli, Terry, Stout & Kraus, LLP

(57) ABSTRACT

To control information obtained from inside of a living body with higher precision as compared to that in the conventional technology by controlling a ratio of intensities of light, directed to a trial body, in a plurality of wavelength ranges different in peak wavelength from each other, a measurement error included in information obtained from the living body can be controlled by changing a ratio of intensity of the light in the first wavelength range against that of the light in the second wavelength range. When intensity of irradiated light is limited from the viewpoint of safety to the trial subject, keeping a ratio of the light irradiated to the trial body in the first wavelength range against that of the light in the second wavelength range under a prespecified value and also changing the ratio of irradiated light intensities under the prespecified value.

6 Claims, 14 Drawing Sheets

○ : IRRADIATED POSITION
● : LIGHT-DETECTED POSITION
▤ : MEASURED POSITION

○ : IRRADIATED POSITION
● : LIGHT-DETECTED POSITION
▤ : MEASURED POSITION

PEAK WAVELENGTH OF LIGHT IN A
FIRST WAVELENGTH RANGE (nm)
(PEAK WAVELENGTH OF LIGHT IN A
SECOND WAVELENGTH : 830 nm)

IRRADIATION INTENSITY OF SECOND LIGHT ASSUMING THAT TOTAL IRRADIATION INTENSITY WITH FIRST LIGHT (WITH A PEAK AT 782 nm) AND SECOND LIGHT (WITH A PEAK AT 830 nm) IS 2

IRRADIATION INTENSITY OF SECOND LIGHT ASSUMING
THAT TOTAL IRRADIATION INTENSITY WITH FIRST LIGHT
(WITH A PEAK AT 692 nm) AND SECOND LIGHT
(WITH A PEAK AT 830 nm) IS 2

IRRADIATION INTENSITY OF SECOND LIGHT ASSUMING
THAT TOTAL IRRADIATION INTENSITY WITH FIRST LIGHT
(WITH A PEAK AT 692 nm) AND SECOND LIGHT
(WITH A PEAK AT 830 nm) IS 2

US 7,991,447 B2

BIOLOGICAL PHOTOMETRIC EQUIPMENT

FIELD OF THE INVENTION

The present invention relates to biological photometric equipment, and more specifically to biological photometric equipment for optically measuring information in an organism, especially changes in density of a light-absorbing material.

BACKGROUND OF THE INVENTION

It is possible to noninvasively acquire information inside an organism by using light having high transmittance to an organism and also having light intensity peak wavelength (described as peak wavelength hereinafter) in a range from a visual area to a near-infrared area. This technique is based on the Lambert-Beer law indicating that an logarithmic value of a detected optical signal is proportional to a product of a light path length by density. Based on this law, for instance, the technique has been developed for measuring relative changes in density of "oxygenated hemoglobin (Hb)" and "deoxygenated Hb" in an organism. Hb is a substance present in an erythrocyte and important for delivering oxygen, and shows different light absorption spectrums when the substance fetches in oxygen and when the substance releases oxygen respectively (refer to FIG. 2). Therefore, by using two types of light having respective different wavelength ranges and measuring changes in transmitted light amplitude of light in each wavelength band ($\Delta A_{(\lambda 1)}$, $\Delta A_{(\lambda 2)}$), changes in density of oxygenated Hb and deoxygenated Hb ($\Delta C_{oxy}$, $\Delta C_{deoxy}$) can be computed from Equation (1) below. In the equation, $\epsilon_{oxy}$ and $\epsilon_{deoxy}$ indicate an absorption constant of oxygenated hemoglobin and an absorption constant of deoxygenated hemoglobin, respectively, in each wavelength band.

$$\Delta C_{oxy} = \frac{-\varepsilon_{deoxy(\lambda 2)} \cdot \Delta A_{(\lambda 1)} + \varepsilon_{deoxy(\lambda 1)} \cdot \Delta A_{(\lambda 2)}}{E}$$
$$\Delta C_{deoxy} = \frac{\varepsilon_{oxy(\lambda 2)} \cdot \Delta A_{(\lambda 1)} - \varepsilon_{oxy(\lambda 1)} \cdot \Delta A_{(\lambda 2)}}{E}$$
$$E = \varepsilon_{deoxy(\lambda 1)} \cdot \varepsilon_{oxy(\lambda 2)} - \varepsilon_{deoxy(\lambda 2)} \cdot \varepsilon_{oxy(\lambda 1)}$$
(1)

Changes in the state of oxygen in an organism can be obtained from changes in the densities of oxygenated Hb and deoxygenated Hb, and therefore Hb is used as an index material for oxygen present in a brain. Devices for measuring changes in the density of Hb in an organism are disclosed, for instance, in Patent Documents 1 and 2. Efficacy of these devices is described, for instance, by Atsushi Maki et al. (refer to Non-patent document 1). This document discloses measurement of functions of a human brain by measuring changes in Hb density in the cerebral cortex. More specifically, in association with activation of sensory functions and motor functions of a human, a quantity of blood in cerebral cortex areas controlling the functions locally increases, and therefore activity conditions of a human brain can be assessed by detecting changes in densities of oxygenated Hb or deoxygenated Hb in the areas.

Patent Document 1: Japanese Patent Laid-open No. 9-149903
Patent Document 2: Japanese Patent Laid-open No. 9-98972
Non-patent Document 1: Medical Physics, 22, 1997-2005 (1995)
Non-patent Document 2: Medical Physics, 28(6), 1108-1114 (2001)

SUMMARY OF THE INVENTION

In the biological photometric technique as described above for measuring a plurality of light-absorbing materials (such as oxygenated Hb and deoxygenated Hb) in an organism using light having a plurality of wavelength ranges with peak wavelengths different from each other, generally additive averaging is required to be performed several times for detecting minute changes in density of a light-absorbing material. The reason is that when an amplifier is used to detect weak transmitted light (sometime also described as reflected light), also device noises other than a biological signal to be measured increase, and a measurement error may occur which is relatively larger as compared with changes in densities of measured Hb ($\Delta C_{oxy}$, $\Delta C_{deoxy}$) Generally, the measurement noises decrease in proportion to an inverse number of a square root of the number of times of addition, and therefore the number of times of addition to be required is determined according to a signal/noise ratio in each measurement step. Thus, when it is necessary to reduce the measurement error to a half ($\frac{1}{2}$), the number of times of addition as large as four times is required.

FIGS. 3A and 3B illustrate examples of a measurement error of a change in deoxygenated Hb density. Both FIG. 3A and FIG. 3B illustrate measurements of changes in deoxygenated Hb density in a frontal cortex performed by giving the same stimuli to the same trial subject. In FIG. 3A, the number of times of addition is four, while that in FIG. 3B is sixteen, so that a measurement error in FIG. 3B is about a half of a measurement error in FIG. 3A. For instance, in measurement of cerebral functions as described above, to abstract signals (for changes of oxygenated Hb and deoxygenated Hb associated with brain activities), additive averaging of about 10 measurement values is generally required. As the number of times of addition increases, a period of time required for measurement becomes longer and a load to a trial subject becomes more serious. Therefore, reduction of a measurement error is desired to enable signal detection with the minimum number of times of addition.

The measurement error as used herein indicates noises caused by devise noises included in changes of measured Hb densities, and is determined by the following two factors.

One is device noises dependent on the gain described above, and the device noises are included in a transmitted light signal. Therefore, the noises are sometimes referred to as transmitted light noises. The noises depend on irradiation intensity determining the transmitted light intensity. When the transmitted light intensity is low, it is necessary to raise a gain in detection, which increases the transmitted light noises. Therefore it is desirable to raise intensity of irradiated light in order to provide the maximum transmitted light. However, when safety to an organism is taken into consideration, it is impossible to raise the irradiation intensity infinitely.

Another factor relates to an absorption constant of oxygenated Hb and that of deoxygenated Hb used in the equation (1) for calculating changes in Hb densities. The absorption constants depend on a wavelength.

Yuichi Yamashita et al. discloses (in Non-patent document 2) that, when changes in density of oxygenated Hb ($\Delta C_{oxy}$) and those of deoxygenated Hb ($\Delta C_{deoxy}$) are to be measured using light in two wavelength ranges (having peak wavelengths in $\lambda 1$, $\lambda 2$), two factors determine the measurement errors: one is the device noises included in a transmitted light signal for light in each wavelength range (transmitted light noises: $\delta \Delta A_{(\lambda 1)}$, $\delta \Delta A_{(\lambda 2)}$); the other is an absorption constant of the oxygenated Hb ($\epsilon_{oxy(\lambda 1)}$ and $\epsilon_{oxy(\lambda 2)}$) and that of the deoxygenated Hb ($\epsilon_{deoxy(\lambda 1)}$ and $\epsilon_{deoxy(\lambda 2)}$). In the measurement of Hb density changes using two types of light in respective different wavelength ranges, a measurement error is calculated through the following equation (2) derived from the law of propagation of errors:

$$(\delta \Delta C_{oxy})^2 = \left(\frac{-\varepsilon_{deoxy(\lambda 2)}}{E}\right)^2 (\delta \Delta A_{(\lambda 1)})^2 + \left(\frac{\varepsilon_{deoxy(\lambda 1)}}{E}\right)^2 (\delta \Delta A_{(\lambda 2)})^2$$

$$(\delta \Delta C_{deoxy})^2 = \left(\frac{\varepsilon_{oxy(\lambda 2)}}{E}\right)^2 (\delta \Delta A_{(\lambda 1)})^2 + \left(\frac{-\varepsilon_{oxy(\lambda 1)}}{E}\right)^2 (\delta \Delta A_{(\lambda 2)})^2$$

$$E = \varepsilon_{deoxy(\lambda 1)} \cdot \varepsilon_{oxy(\lambda 2)} - \varepsilon_{deoxy(\lambda 2)} \cdot \varepsilon_{oxy(\lambda 1)}$$

(2)

As suggested by the equation (2) above, when the transmitted light noises ($\delta \Delta A_{(\lambda 1)}$, $\delta \Delta A_{(\lambda 2)}$) in the wavelength ranges are equal to each other, as a different between absorption constants of hemoglobin in the wavelength range becomes larger (that is, as a difference between the wavelengths becomes longer), the measurement error becomes smaller. The example is shown in FIG. 4. FIG. 4 shows relative values of measurement errors for the hemoglobin in a case where the transmitted light noises ($\delta \Delta A_{(\lambda 1)}$, $\delta \Delta A_{(\lambda 2)}$) of light in the wavelength range is kept at constant levels, a peak wavelength of light in a first wavelength range is gradually changed from 650 nm to 800 nm, a peak wavelength of light in a second wavelength range is set to 830 nm, and the light obtained by mixing the two types of light described above is directed to a trial subject. As a wavelength of light in the first wavelength range to be combined with the light in the second wavelength range becomes shorter, a difference between absorption constants of Hemoglobin for light in the two wavelength ranges becomes larger, and therefore a measurement error for the two types of hemoglobin becomes smaller.

In practice, however, amplitudes of transmitted light noises vary according to a trial subject or a wavelength of irradiated light, so that the tendency shown in FIG. 4 is not always realized as it is.

Amplitude of transmitted light noises is determined by a gain of an amplifier adjusted according to intensity of transmitted light (varying according to a trial subject or a wavelength of irradiated light) (refer to FIG. 5). FIG. 5 suggests that, as a gain of an amplifier is larger, also transmitted light noises become larger proportionately. In other words, the transmitted light noises depend on intensity of transmitted light determined by a mutual reaction between the trial subject and a wavelength of irradiation light, and therefore when living bodies having a remarkable individual difference are to be tested, the noises can hardly be expressed with a simple parameter.

FIG. 6 illustrates measurements of a head region of each of four trial adult subjects, taken as an example in which intensity of transmitted light (transmission factor) varies according to a trial subject as well as to a wavelength of irradiated light. In this example, three regions (an occipital region, a vertex region, and a temporal region) of a head of each trial subject were measured. Assuming that a transmission factor of light having a peak wavelength at 830 nm often used in the conventional types of devices is 1, a transmission factor of light having a peak wavelength at 782 nm little varies, but as the peak wavelength becomes shorter to 750, 692, and 678 nm, the transmission factor will become smaller. Although the general tendency corresponding to a wavelength of irradiated light or a measured region can be recognized, trial subjects have respective individual differences. Thus, it is difficult to generalize the tendency. In other words, it is desired to develop a mechanism capable of reducing a measurement error for each trial subject.

As described above, when the transmission factor becomes smaller, there is no way but to increase a gain of an amplifier up to a level allowing detection of a transmitted light signal, with the result that noises caused by transmitted light from the device increase (See FIG. 5).

The specification for Japanese Patent Application No. 2002-19828 filed in the past by the present application describes organic photometric equipment capable of sensing a different transmission factor for each measured region of a living body and selecting a wavelength of light suited to the region to be measured. The specification also teaches that a measurement error is reduced by changing a wavelength of irradiated light in accordance with a trial subject, but a measurement error can also be reduced by controlling noises caused by transmitted light.

In other words, if it is possible to control intensity of transmitted light in response to attenuation in intensity of the transmitted light and to obtain desired intensity of transmitted light, namely, noises caused by the transmitted light, a measurement error can be controlled.

An object of the present invention is to provide biological photometric equipment capable of acquiring information in a living body with higher precision as compared to that provided by the conventional techniques by controlling intensity of irradiated light in plural wavelength ranges different in peak wavelength with each other.

The present inventor found that, when light in first and second wavelength ranges different in peak wavelength from each other is directed to a trial subject as mixed light, a measurement error for information of a living body as an object for measurement changes according to a ratio of noises caused by each transmitted light (noises caused by transmitted light in the first wavelength range or in the second wavelength range) against the total of noises caused by the transmitted light (in the first and second wavelength ranges).

In brief, because noises caused by transmitted light depend on intensity of irradiated light as described above, it is possible to control a measurement error for living body information by changing a ratio of irradiation intensity of light in a first wavelength range against that of light in a second wavelength range.

When restriction on intensity of transmitted light is introduced from a viewpoint of protection of a trial subject, control is provided so that the total of irradiation intensity of light in a first wavelength range at a region X of the trial subject to which the light is directed and that in a second wavelength range is not higher than a prespecified value, and in this case a measurement error for living body information can be controlled by changing a ratio of intensity of light in the first wavelength range to that in the second wavelength range keeping the total within the prespecified range.

Generally, when changes in densities of oxygenated Hb and deoxygenated Hb are to be measured by using two types of light different in peak wavelength from each other, a combination is used of light having a peak wavelength in the range from 800 nm to 900 nm and light having a peak wavelength in the range from 600 nm to 800 nm. When the wavelength is lower than 600 nm, the irradiated light is substantially absorbed by the oxygenated and deoxygenated hemoglobin, while, when the wavelength is over 900 nm, the irradiated light is substantially absorbed by water, which makes it impossible to obtain sufficient intensity of transmitted light. In biological photometric equipment for measuring changes in densities of oxygenated and deoxygenated hemoglobin making use of a different between a light absorption spectrum of oxygenated hemoglobin and that of deoxygenated hemoglobin, measurement can be performed with a high degree of accuracy by using light having peak wavelengths shorter and longer than about 805 nm which is the isosbestic point (refer to FIG. 2).

Therefore, it is desirable to use light having a peak wavelength in the range from 810 nm to 900 nm as light having a longer peak wavelength. On the other hand, there are several points to be examined for selection of a wavelength of light having a shorter peak wavelength. When using light having a peak wavelength shorter than 650 nm, the irradiated light may substantially be absorbed by the oxygenated and deoxygenated hemoglobin to disable the measurement, but when the wavelength is in the range from 650 nm to 700 nm, a difference between absorption constants for oxygenated and deoxygenated hemoglobin for light having different peak wavelengths becomes larger. Therefore, the light having a wavelength in the range is well suited to high precision measurement (especially, a wavelength in the range from 680 nm to 700 nm is desirable when the transmission factor is taken into consideration). On the other hand, light in a wavelength range from 700 nm to 790 nm (preferably in the range from 740 nm to 790 nm when the transmission factor is taken into consideration) has a high transmission factor in a living body, and the wavelength is closer to that of another light (in the range from 810 nm to 900 nm), so that more stable measurement may be enabled.

Therefore, it is preferable to use light having a peak wavelength in the range from 650 nm to 800 nm, more preferably from 700 nm to 790 nm, as light having a shorter wavelength. When three or more trial subjects are to be measured, it is possible to use three or more types of light with different peak wavelengths in the range from 600 nm to 900 nm as mixed light.

Using the equation (2) for calculating a measurement error for Hb, changes of Hb measurement errors encountered when a ratio of intensity of light in a first wavelength range against that in a second wavelength range was changed was calculated (refer to FIGS. 7 to 10).

For instance, when changes of densities of oxygenated Hb and deoxygenated Hb in a living body are measured by using first light having a peak wavelength at 782 nm and second light having a peak wavelength at 830 nm, measurement error values for changes in densities of oxygenated Hb and deoxygenated Hb change independently in response to a ratio of intensity of the first light against that of the second light (refer to FIG. 7). Under the conditions as described above, when a ratio of intensity of the first light against that of the second light is set to about 0.5:1.5, a measurement error for the oxygenated Hb is minimized. When the ratio of intensity of the first light against that of the second light is set to about 1.2:0.8, a measurement error for the deoxygenated Hb is minimized. In other words, when intensity of light directed to a region X of a living body in a first wavelength range is in the range from 0.3 times (suited to measurement of oxygenated Hb) to 1.5 times (suited to measurement of deoxygenated Hb) that of light in a second wavelength range, high precision measurement can be performed.

Furthermore, when the two types of Hb are measured simultaneously, an optimal ratio of intensities of irradiated light can be determined by using an index reflecting the measurement error levels of the two types of hemoglobin. FIG. 9 illustrates the situation in which the sum of measurement errors for the oxygenated Hb and that for the deoxygenated Hb changes according to a change in a ratio of intensity of the first light to that of the second light (bold line). Assuming that the ratio of intensity of the first light to that of the second light is set to 0.9:1.1, the sum of measurement errors for the two types of Hb is minimized. Furthermore, generally a change rate in a measurement error for the deoxygenated Hb (signal intensity) is smaller than that for the oxygenated Hb, and higher precision measurement is required for the oxygenated Hb; therefore the rate may be set putting the priority in precision of measurement for the deoxygenated Hb. For instance, as illustrated by a thin line in FIG. 9, it is possible to sum a measurement error for the oxygenated Hb and a doubled measurement error for the deoxygenated Hb and use the sum as an index for measurement to attach a doubly higher importance to the precision in measurement for the deoxygenated Hb as compared to that in measurement for the oxygenated Hb. With the index, when a ration of intensity of the first light against that of the second light is set to about 0.8:1.2, the two types of Hb can be measured most effectively.

Similarly, also when first light having a peak wavelength at 692 nm and second light having a peak wavelength at 830 nm are irradiated, levels of measurement errors for the two types of Hb change independently in response to a ratio of intensity of the first light against that of the second light (FIG. 8). The tendency in this case is different from the result shown in FIG. 7, and when the ratio of irradiation intensity of the first light against that of the second light is set to about 0.5:1.5, the measurement error for the oxygenated Hb is minimized. When the ratio of irradiation intensity of the first light against that of the second light is set to about 1.9:0.1, the measurement error for the deoxygenated Hb is minimized. That is, when irradiation intensity of light in a first wavelength range directed to a region X of a trial subject is in the range from 0.3 times (an intensity ratio suited to measurement of the oxygenated Hb) to 19 times (an intensity ratio suited to measurement of the deoxygenated Hb) that of light directed to the region X in a second wavelength range, high precision measurement can be performed at the region X.

When a measurement error for the deoxygenated Hb is minimized, a measurement error for the oxygenated Hb remarkably increases, and therefore, when the two types of hemoglobin are to be measured, the method is effective in which an index obtained by summing the measurement error levels for the two types of hemoglobin is used for determining an optimal ratio between intensities of the two types of light. FIG. 10 illustrates the situation in which the sum of a measurement error for the oxygenated Hb and that for the deoxygenated Hb changes in response to a ratio between the irradiation intensities of the two types of light (bold line). When a ratio of irradiation intensity of the first light against that of the second light is set to about 1.6:0.4, the sum of the measurement errors for the two types of Hb is minimized. FIG. 10 illustrates a case in which an index obtained by summing a measurement error for the oxygenated Hb and a doubled measurement error for the deoxygenated Hb is used to importantly reduce a measurement error for the deoxygenated Hb like in the situation shown in FIG. 9 (thin line in FIG. 10). In this case, when a ratio of irradiation intensity of the first light against that of the second light is set to about 1.2:0.8, the two type of Hb can be measured most effectively. As described above, also when the sum of irradiation intensities is kept at a constant level, a measurement error included in information for a living body as an object for measurement can more effectively be reduced by changing the ratio between the irradiation intensities of the two types of light.

In summary, light having a peak wavelength in a first wavelength range from 650 nm to 800 nm and light having a peak wavelength in a second wavelength range from 810 nm to 900 nm are mixed to obtain mixed light and the mixed light is irradiated to a trial subject. In this case, irradiation intensity of light in the first wavelength range directed to a region X of a trial subject is in the range from 0.3 times (an intensity ratio suited to measurement of the oxygenated Hb) to 19 times (an intensity ratio suited to measurement of the deoxygenated Hb) that of light in the second wavelength range directed to the region X, whereby high precision measurement can be performed.

In this case, it is generally possible to reduce a measurement error by selecting a wavelength range of each light to shift a ratio of intensity of light in the first wavelength range directed to a measured region of a trial subject against that of light in the second wavelength range from 1:1 as described above. Practically, when irradiation intensity of light in the first wavelength range directed to the region X is in the range from 0.3 to 0.7 time, or 1.3 to 19 times irradiation intensity of light in the second wavelength range, high precision measurement can be performed.

In particular, when a peak wavelength of the light in the first wavelength range is in the range from 700 nm to 790 nm, high precision measurement can be performed by irradiating the region X with light in the first wavelength range with intensity in the range from 0.3 to 0.7 time, or in the range from 1.3 to 10 times intensity of the light in the second wavelength range.

The equipment according to the present invention is characterized by having a computing section for computing a measurement error included in information obtained from a living body as an object for measurement. The measurement error is calculated as a standard deviation of data from which large fluctuations are removed by fitting, or as intensity in a high frequency area which can easily be discriminated from a signal from the living body by means of Fourier transformation.

To estimate a ratio of intensity of light in the first wavelength range against that in the second wavelength range required to realize a desired measurement error, at first the light in the first wavelength range and light in the second ware are directed at any intensity to a trial subject for testing. Then, changes in HB densities are calculated from the intensities of transmitted light and absorption constants detected in the test by applying the equation (1) above. The measurement error is calculated from the changes in the Hb densities by means of the fitting method described or the like. Based on the measurement error obtained in test irradiation as described above, a ratio of light in the first wavelength range to that in the second wavelength range required for realizing the desired measurement error is calculated.

Furthermore, a mechanism for adjusting the irradiated light intensity ratio to the desired value is required. FIG. 15 is a flow chart illustrating a process procedure from setting a desired measurement error to the practical measurement.

With the equipment according to the present invention, for instance, when a measurement object is specified to acquire information on either the oxygenated Hb or deoxygenated Hb, an irradiated light intensity ratio can be calculated to reduce the measurement error as much as possible. Therefore, precision in measurement can be improved by adjusting irradiation intensities of pieces of light each having a different peak wavelength so that the light irradiation intensity ratio suited to acquire information from the living body can be obtained.

Furthermore, when information on both a first living thing and a second living thing are to be acquired with high precision, assuming that sign a denotes a ratio of intensity of light in a first wavelength range directed to a region X of a trial subject against that in a second wavelength range substantially minimizing a measurement error included in information concerning a first measure living body and also that sign b denotes a ratio of intensity of light in a first wavelength range directed to the region X of a trial subject against that in a second wavelength range substantially minimizing a measurement error included in information concerning a second living body, by directing the light changing the light irradiation intensity from time to time between a and b, measurement errors included in information concerning all of the living bodies can substantially be reduced at most.

DETAILED DESCRIPTION OF THE PREFERRED EMBODIMENT

An embodiment of the present invention will be described below. In this embodiment, for measurement of changes in densities of oxygenated Hb and deoxygenated Hb in a living body, two types of light different in peak wavelength from each other are used to set a light irradiation position and a light receiving position at respective positions. The same measurement can be performed even when the number of wavelength ranges of irradiated light and of positions for irradiation and receiving light are increased.

Figure 16:
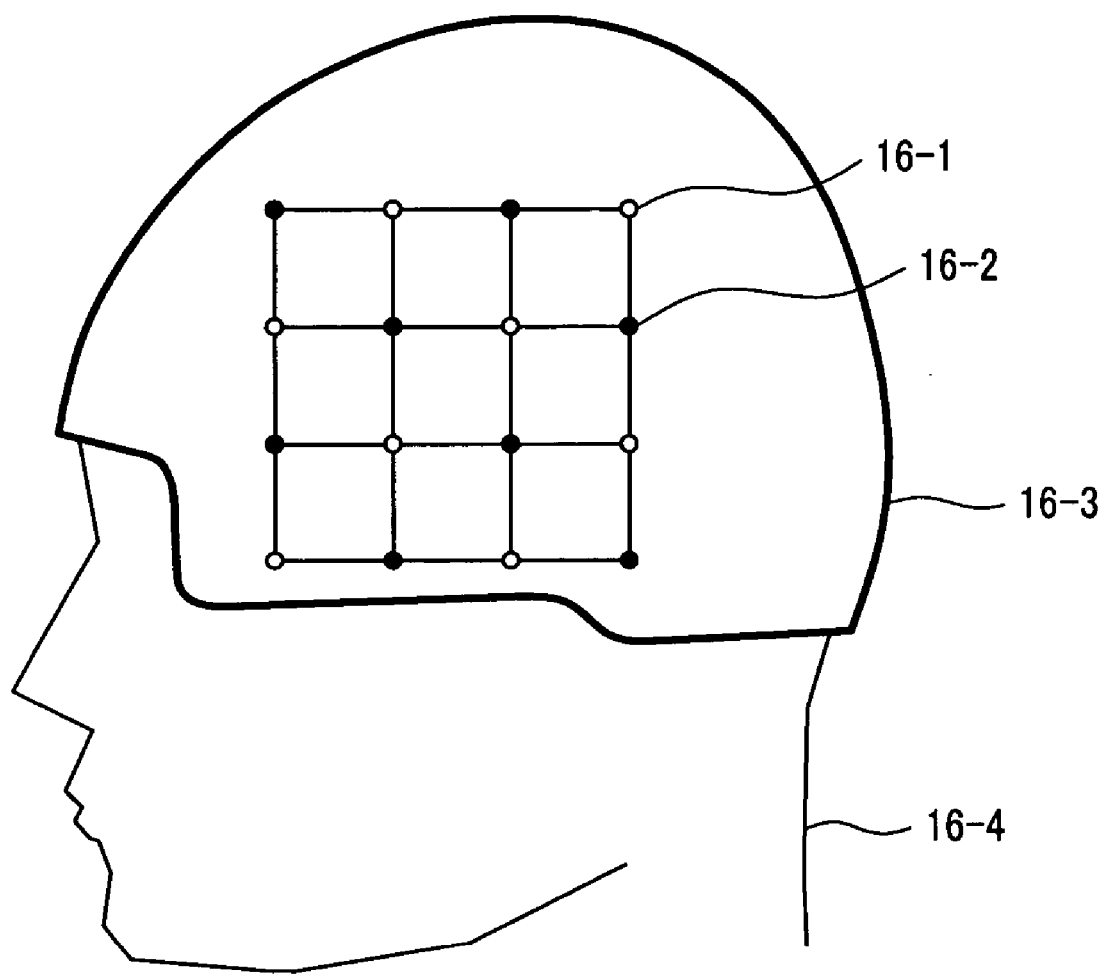
FIG. 16 is a diagram illustrating an example in which regions to be measured are defined in lattice form on a trial subject, light irradiating units and light receiving units are alternately arranged on nodes of the lattice, and also they are fixed to a helmet-like anchoring tool attachable onto the head of the trial subject.

FIG. 16 illustrates a case in which regions to be measured are defined on a trial subject in lattice form and light irradiating units and light receiving units are alternately arranged on nodes of the lattice. A helmet-like anchoring tool 16-3 is set on a trial subject 16-4 and optical fibers for light irradiating units 16-1 and light receiving units 16-2 arranged in lattice form are fixed to holes provided in the anchoring tool. With this configuration, changes in densities of oxygenated Hb and deoxygenated Hb in the trial subject can be measured at multiple points.

Furthermore, by increasing the number of wavelength ranges of light directed to a trial subject, it is possible to measure not only changes in densities of oxygenated Hb and deoxygenated Hb, but also changes in densities of other light-absorbing materials such as cytochrome or myoglobin.

Figure 1:
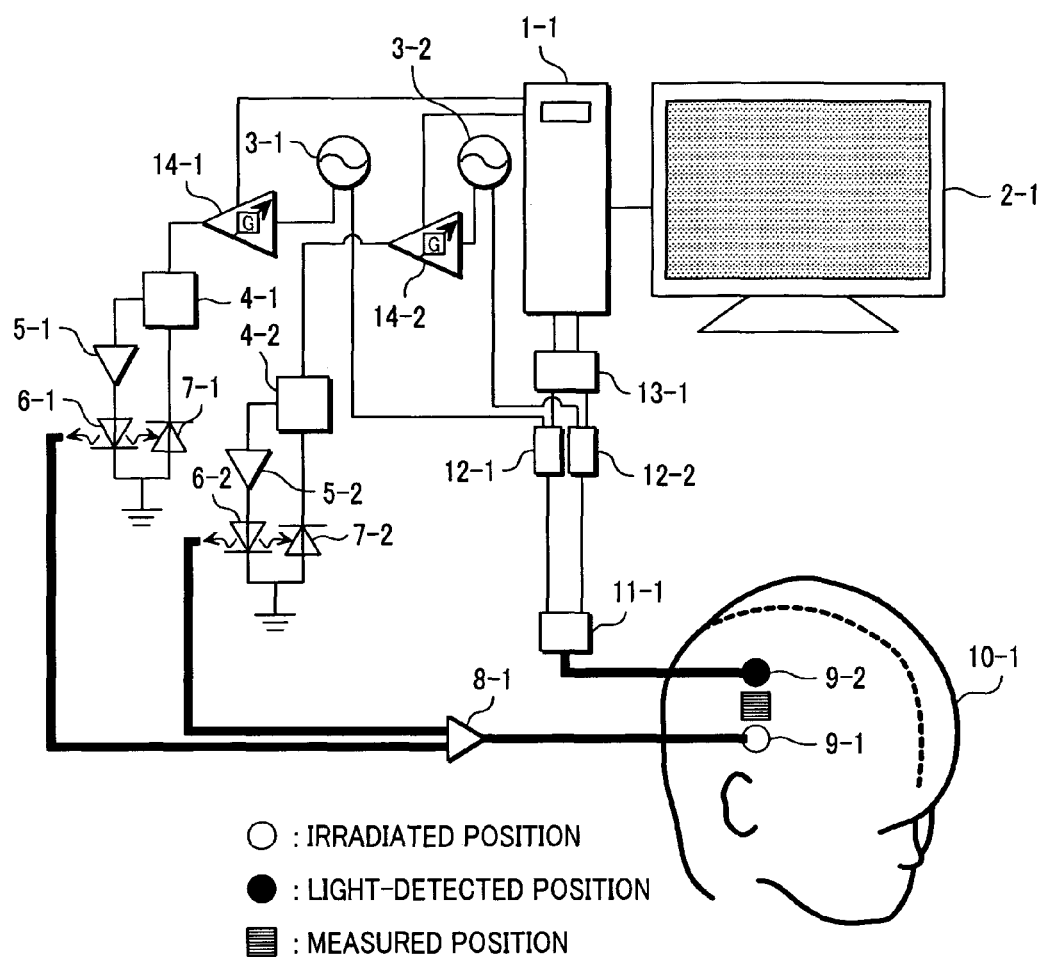
FIG. 1 is a block diagram illustrating a configuration of biological photometric equipment according to an embodiment of the present invention.
Figure 2:
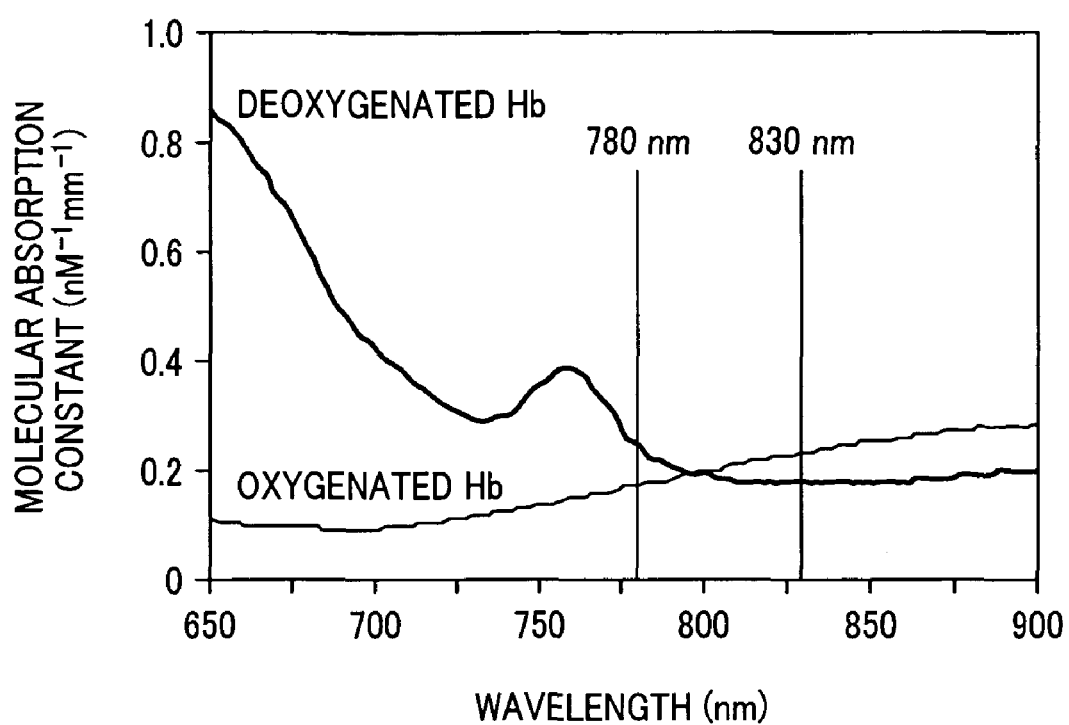
FIG. 2 illustrates absorption spectrums for oxygenated Hb and deoxygenated Hb.
Figure 3A:
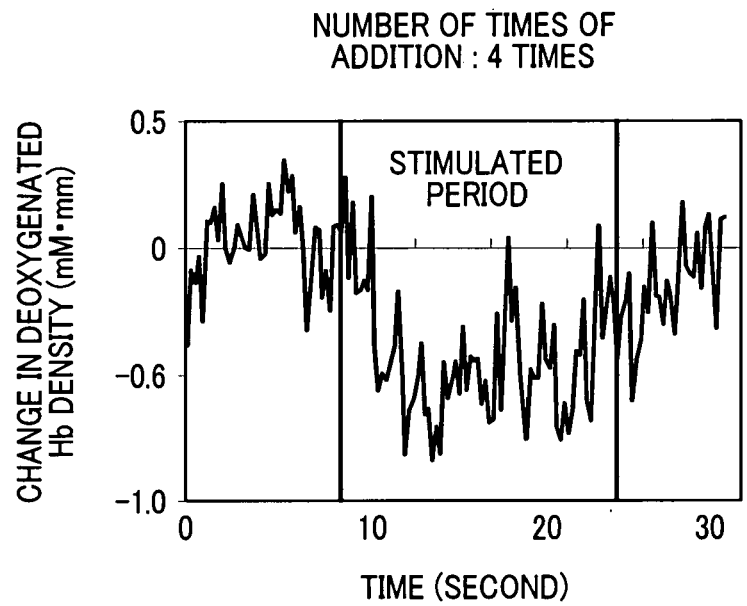
FIGS. 3A and 3B illustrate examples of measurement errors in measurement of a change in density of deoxygenated Hb.
Figure 3B:
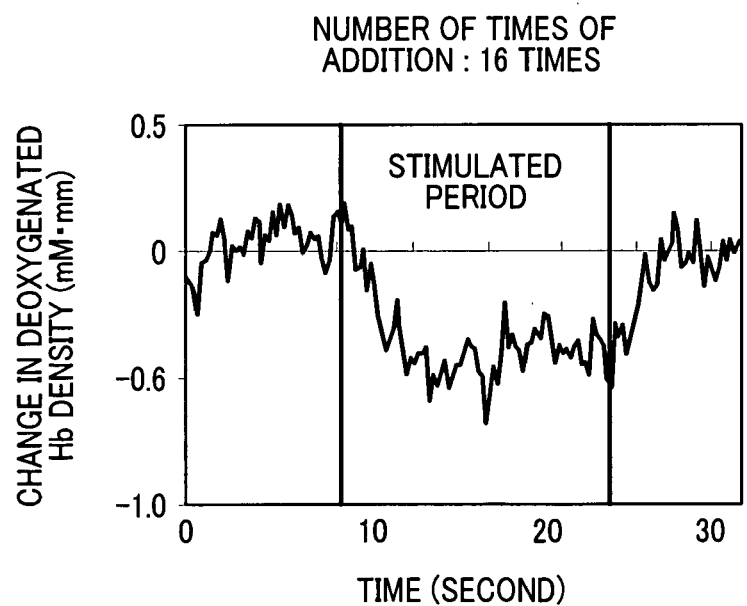
Figure 4:
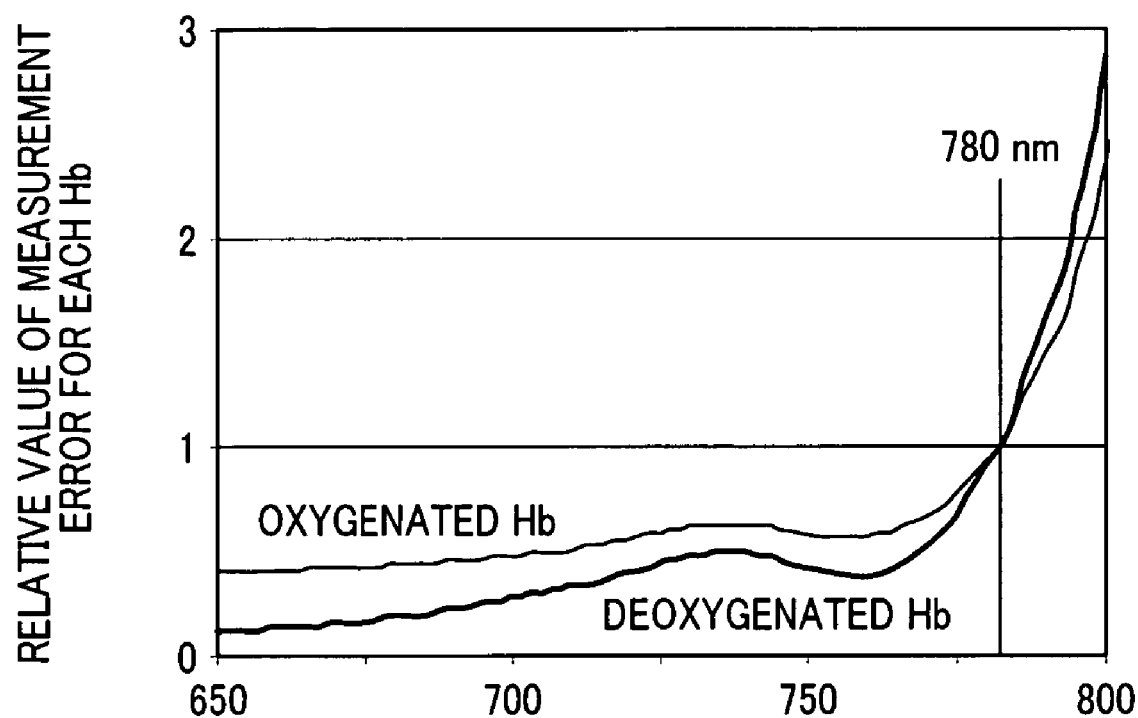
FIG. 4 illustrates the relationship between measurement errors for oxygenated Hb and deoxygenated Hb calculated through the equation for error propagation and peak wavelengths of irradiated light.
Figure 5:
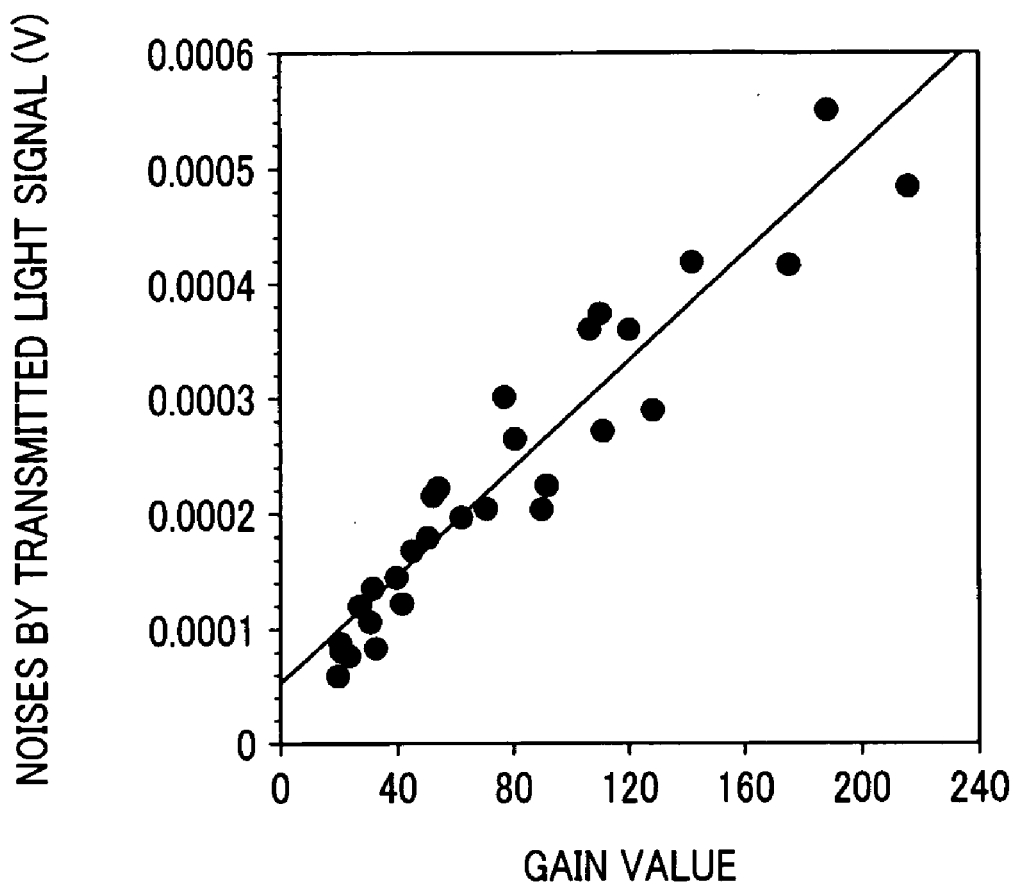
FIG. 5 illustrates the relationship between a gain of an amplifier and noises caused by transmitted light.
Figure 6:
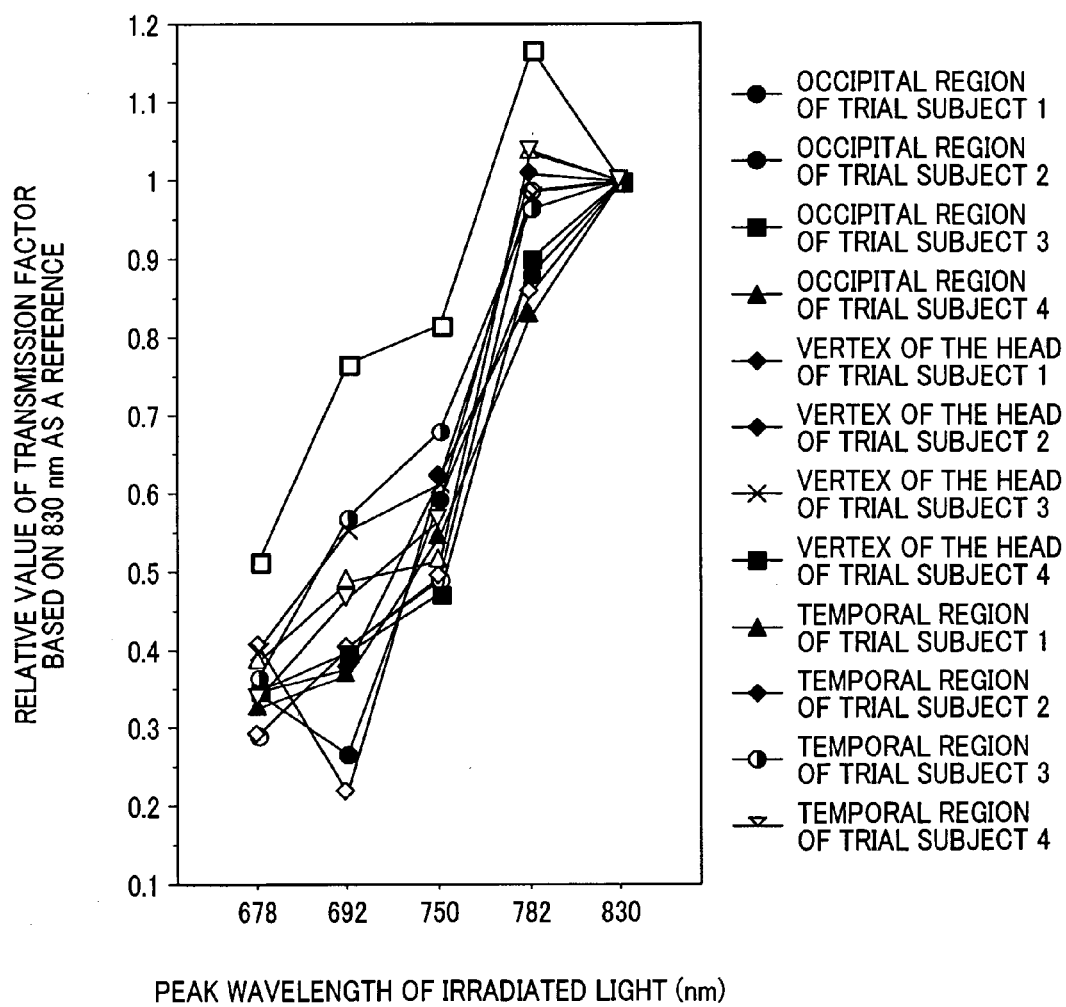
FIG. 6 illustrates the relationship between a transmission factor and a peak wavelength of irradiated light.
Figure 7:
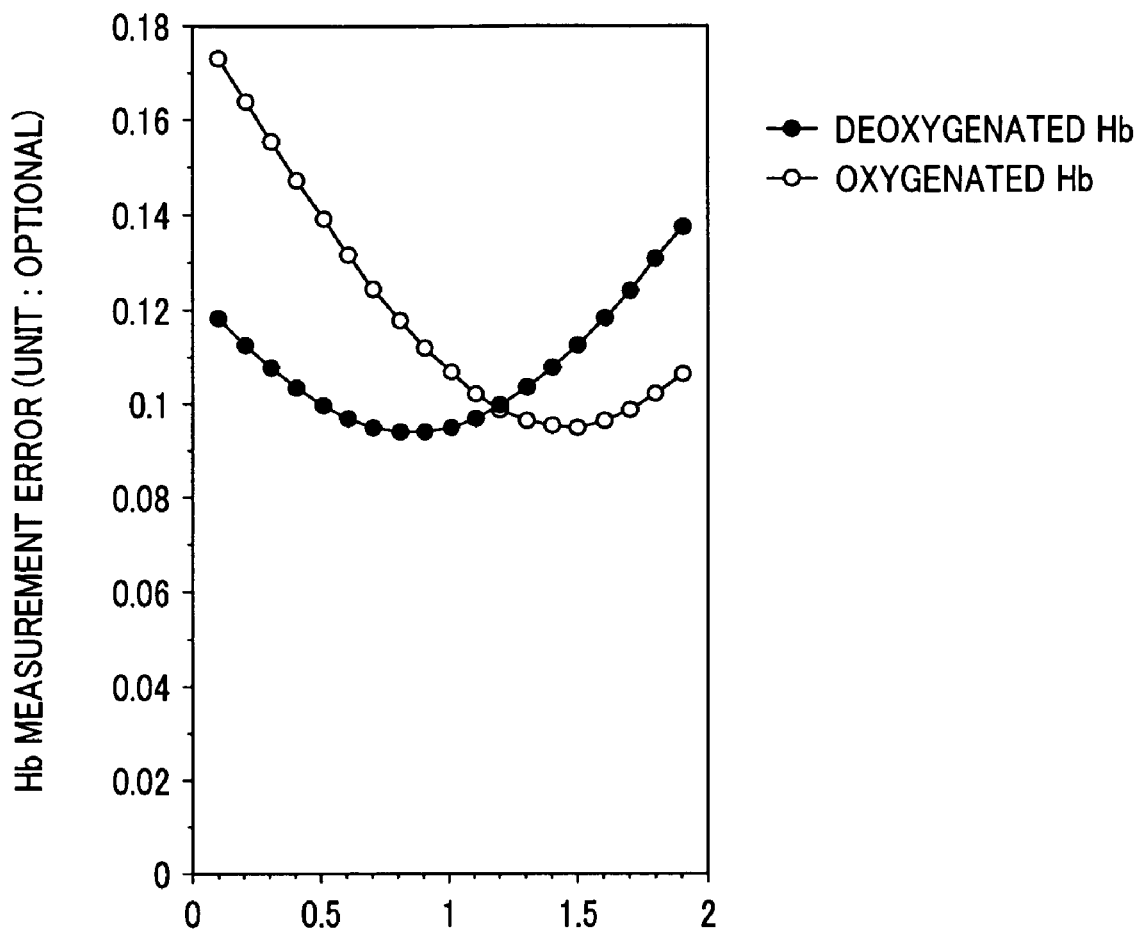
FIG. 7 illustrates the relationship, in a measurement using light in a first wavelength range having a peak wavelength at 782 nm and light in a second wavelength range having a peak wavelength range at 830 nm, between a ratio between intensities of the irradiated light in the wavelength ranges and measurement errors for oxygenated Hb and deoxygenated Hb.
Figure 8:
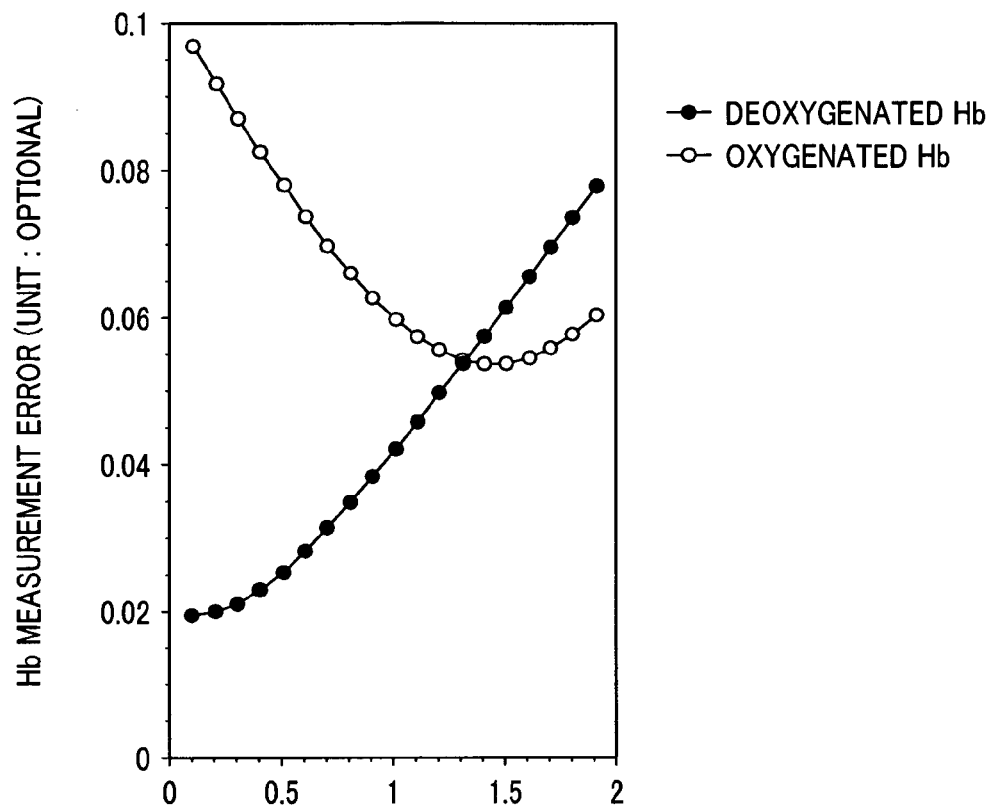
FIG. 8 illustrates the relationship, in a measurement using light in a first wavelength range having a peak wavelength at 692 nm and light in a second wavelength range having a peak wavelength range at 830 nm, between a ratio between intensities of the irradiated light in the wavelength ranges and measurement errors for oxygenated Hb and deoxygenated Hb.

FIG. 1 illustrates an example of a configuration of equipment according to the present invention. The equipment according to this embodiment includes a control unit 1-1 comprising an electronic computer represented by a personal computer or a work station; a display device 2-1 connected to the controller; a laser diode 6-1 with a peak wavelength 6-2 at the wavelength .lamda.1 and a laser diode with a peak wavelength at the wavelength .lamda.2; monitor photodiodes 7-1 and 7-2 provided close to the laser diodes 6-1 and 6-2, respectively; oscillators 3-1 and 3-2 for generating signals for modulating the two laser diodes at different frequencies, respectively; amplifiers 14-1 and 14-2 for varying an amplitude of an oscillator signal and a DC bias level; APC (auto power control, automatic light volume control) circuits 4-1, 4-2 for controlling a current value loaded to the laser diodes with driver circuits 5-1 and 5-2 so that a signal level from the monitor photodiode is the same as that of a signal from the oscillator; a light mixer 8-1 for mixing light in two wavelength ranges different in peak wavelength from each other; a light irradiating unit 9-1 for irradiating a head skin of a trial subject 10-1 with light from the light mixer 8-1 via an optical fiber; a light receiving unit 9-2 provided so that a tip of the optical finer for detection of light is located at a position away from the light irradiating unit (30 mm away in this embodiment); light detectors 11-1 capable of detecting each light; lock-in amplifiers 12-1 and 12-2 for receiving modulated frequencies from the oscillators as reference signals; and an analog/digital converter for converting a signal for transmitted light in each wavelength range outputted from the lock-in amplifier to an analog signal. Measurement is performed at a substantially intermediate position between the light irradiating unit 9-1 and the light receiving unit 9-2.

In this embodiment, one light irradiating unit and one light receiving unit are provided, but a plurality of light irradiating units and a plurality of light receiving units may be provided. For instance, in a configuration in which light irradiating units and light receiving units are alternately provided, measurement is performed at a substantially intermediate position between a light irradiation position and a light receiving position adjacent to the light irradiation position. Although an oscillator is used for separating a plurality of signals from each other in this embodiment, optical signals can be separated from each other not using an oscillator and using pulsed light and according to the lighting timing.

The light in two wavelength ranges different in peak wavelength from each other mixed by the mixer 8-1 are directed by the light irradiating unit 9-1 to a prespecified position, collected from a light receiving position adjacent thereto by the light receiving unit 9-2, and is subjected to photoelectric conversion by the light detector 11-1. The light detector 11-1 detects light reflected and scattered inside the trial subject and returned thereto and converts the light to an electric signal, and for instance, a photoelectric conversion element such as an avalanche photoelectric conversion element is used. The transmitted light signal subjected to photoelectric conversion by the light detector 11-1 is inputted to the lock-in amplifiers 12-1, 12-2, and are separated from each other according to the different two peak wavelengths. The transmitted light signals for two types of light different in peak wavelength with each other are separated by the lock-in amplifiers 12-1, 12-2 having received modulated frequencies as reference frequencies from the oscillators 3-1, 3-2. However, even when two or more types of light different in peak wavelength from each other are used and there are a plurality of positions for irradiation, by using a substantially large number of modulated frequencies and inputting the modulated frequencies as reference frequencies to the lock-in amplifiers respectively, intensity of transmitted light can be separated according to each wavelength and to a position of each light source. The transmitted light signals outputted from the lock-in amplifiers are subjected to analog/digital conversion by the analog/digital converter 13-1 and are inputted to the control unit 1-1. Changes in densities of hemoglobin at each region for measurement and the associated measurement error are calculated based on the transmitted light signals stored in the control unit 1-1.

The measurement error is defined as a fluctuation of a signal generated independently of information of a living body, and is expressed, for instance, with a standard deviation of signals in the stable state. For removal of the fluctuation originated from a loving body and extracting only noises originated from the equipment, a band-pass filter or the like may advantageously be used.

Intensities of light irradiated from the laser diodes 6-1 and 6-2 are controlled according to the following procedure. The control unit 1-1 has a mechanism used by a user to set control parameters on the operation screen. In this embodiment, the control parameters are output amplitude values from the amplifiers 14-1 and 14-2 and DC bias levels, and the control unit 1-1 controls gains of the amplifiers 14-1, 14-2 and the DC bias levels according to a value inputted by a measuring person.

When output amplitudes from the amplifiers 14-1 and 14-2 increase, outputs from the laser diodes 6-1, 6-2 increase via the APC circuits 4-1, 4-2. Similarly an average level of outputs from the laser diodes is set by adjusting the DC bias levels in the amplifiers 14-1 and 14-2. Usually it is required only to set a DC bias level so that a modulation degree of the optical signal is set to 1, and the setting can be performed automatically by inputting only the amplitude. The APC circuits 4-1, 4-2 has band ranges responding to frequencies of the oscillators 3-1, 3-2.

A desired value of a measurement error level or signal noise ratio or a desired range of the values thereof may be set as a control parameter. In this case, a measurement error level or a ratio of signal noises is derived from the measurement error calculated using the control unit 1-1 according to the procedure described above, and gains of and DC bias levels in the amplifiers 14-1, 14-2 are automatically set so that the desired value will be obtained or the obtained value will fall in the desired range. Similarly, intensity of light irradiated to a living body may be inputted and set as a control parameter.

The adjustments described above are performed each time when the light irradiating unit 9-1 and the light detecting unit 9-2 is set on the trial subject 10-1. Needless to say, the adjusting operations may be performed step by step before start of measurement.

In the embodiment described above, a laser diode controlled by an APC is used as a light source, but even when a laser diode driven by an ACC (automatic current control) circuit, the same control can be performed by changing the circuit configuration.

Descriptions are provided below about a method of setting intensities of irradiated light in wavelength ranges different in peak wavelength from each other with reference to an example of the operation screen (refer to FIGS. 11 to 13). When a plurality of light irradiating units and light receiving units are provided to execute measurement at a plurality of respective positions, the setting may be changed for each position for measurement as described below.

Figure 11:
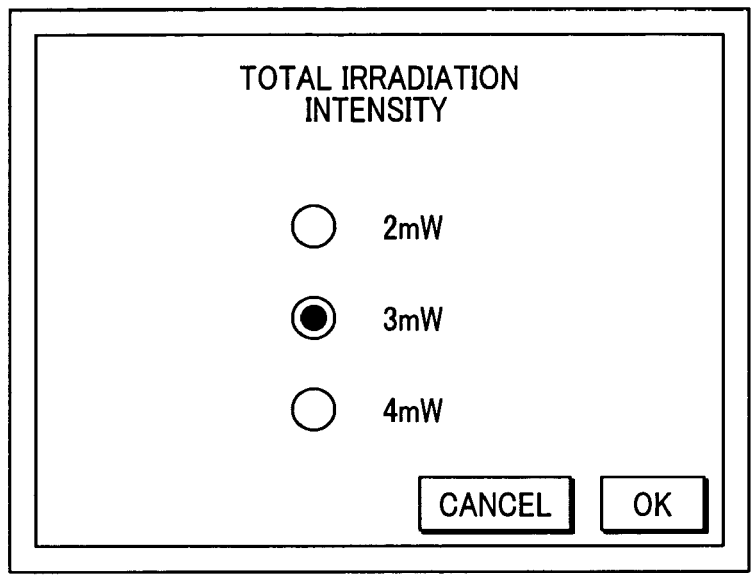
FIG. 11 a diagram illustrates an example of an operation screen used for setting intensities of light in first and second wavelength ranges.

FIG. 11 illustrates an example of a screen used for setting the sum of intensities of irradiated light. From the viewpoint of safety, intensity of light directed to a living body should be kept under a prespecified value, but the reference value varies according to each trial subject. For instance, irradiated light with different intensities should be used for an adult and an infant as trial subjects to efficiently perform measurement. Therefore, the screen used by a user to sum intensities of irradiated light as shown in FIG. 11 is effective.

Figure 12:
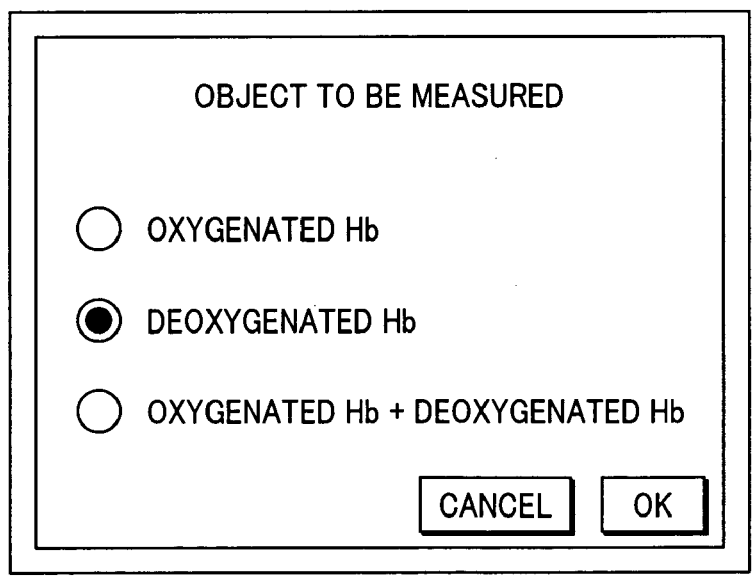
FIG. 12 is a diagram illustrating an example of an operation screen used for selecting information on a living body as a measurement object.

FIG. 12 is a screen showing light-absorbing materials in a living body which can be measured in this embodiment (oxygenated Hb, deoxygenated Hb, oxygenated Hb+deoxygenated Hb), and this screen is used by a user to select an object for measurement by pressing a radio button provided on the left side of each item. The selection is decided by selecting any object for measurement and pressing the OK button displayed on the right bottom of the screen.

When a single object for measurement such as the oxygenated Hb or deoxygenated Hb is set, a ratio between intensities of light in wavelength ranges different in peak wavelength from each other is automatically adjusted so that a measurement error for the selected object for measurement will be minimized.

Figure 9:
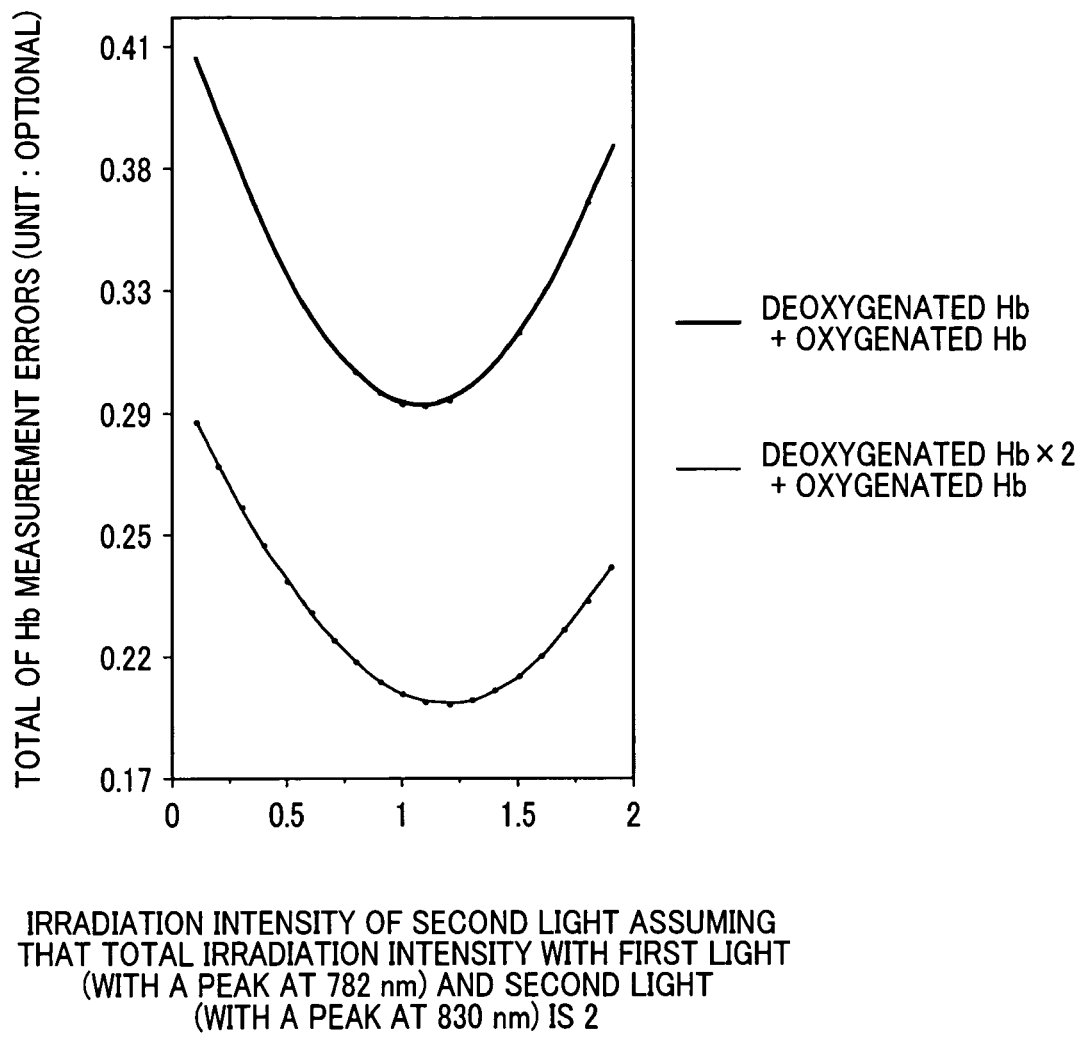
FIG. 9 illustrates the relationship, in a measurement using light in a first wavelength range having a peak wavelength at 782 nm and light in a second wavelength range having a peak wavelength range at 830 nm, between a ratio between intensities of the irradiated light in the wavelength ranges and a total measurement error (the sum between a measurement error for oxygenated Hb and that for deoxygenated Hb)
Figure 10:
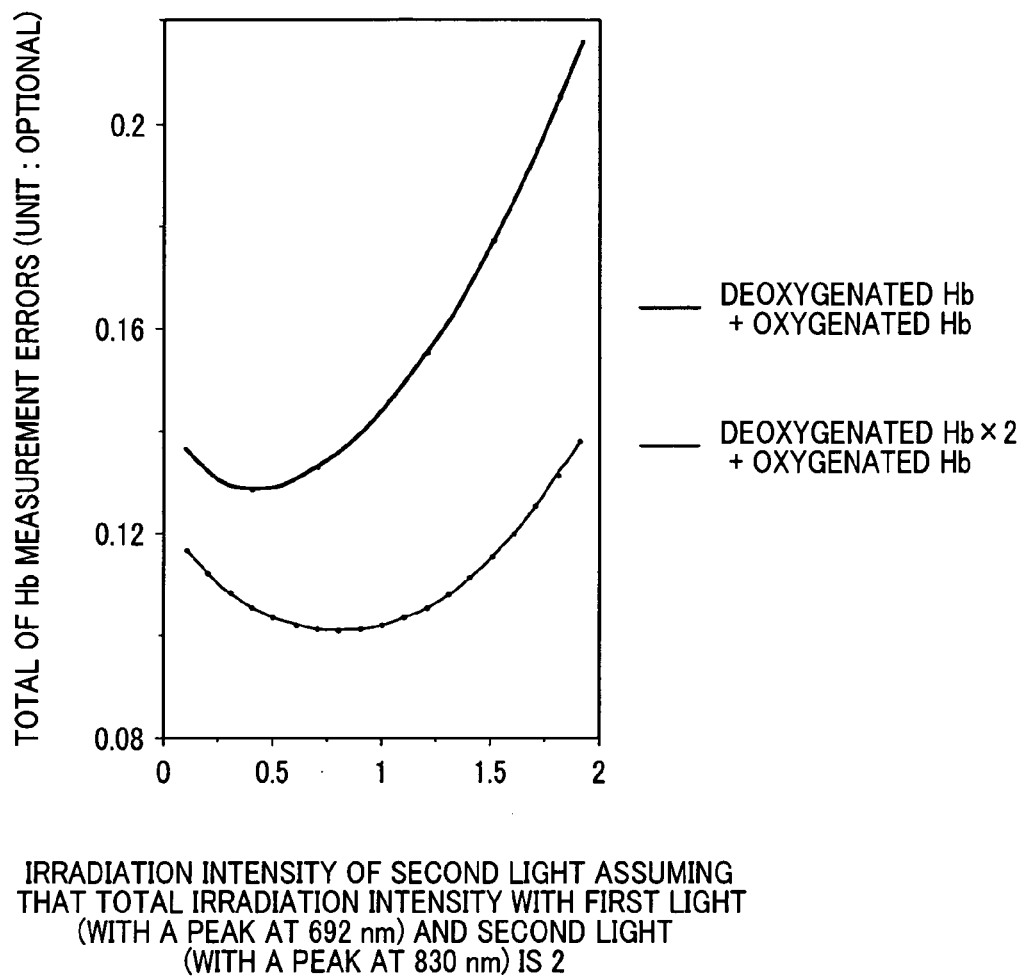
FIG. 10 illustrates the relationship, in a measurement using light in a first wavelength range having a peak wavelength at 692 nm and light in a second wavelength range having a peak wavelength range at 830 nm, between a ratio between intensities of the irradiated light in the wavelength ranges and a total measurement error (the sum between a measurement error for oxygenated Hb and that for deoxygenated Hb)
Figure 13:
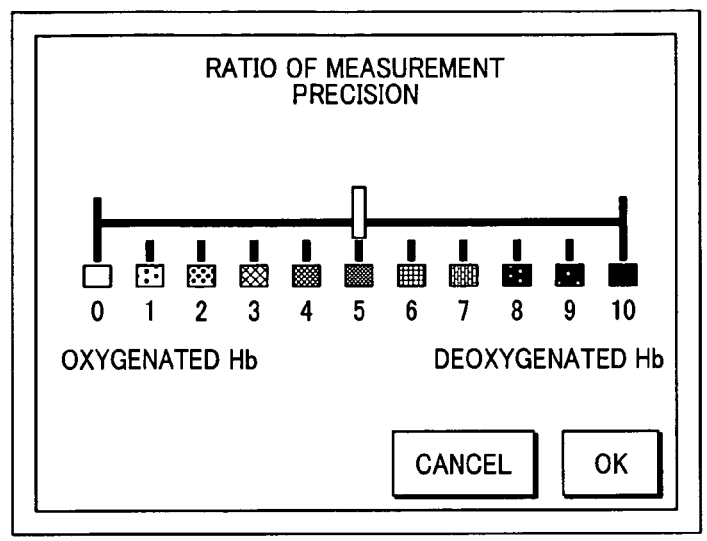
FIG. 13 is a diagram illustrating an operation screen used for setting a ratio between measurement precisions for a plurality of pieces of information on a living body as a measurement object.

When a plurality of measurement objects such as oxygenated Hb+deoxygenated Hb are selected as shown in FIG. 13, a screen used for setting a ratio of measurement precisions according to importance of each measurement object is prepared. When each Hb is to be measured at the same precision, the ratio of intensities of irradiated light is adjusted by setting a slide bar switch shown in FIG. 13 at the central position so that the measurement precision for the two types of Hb will be identical (refer to bold lines in FIGS. 9 and 10). When it is desired to measure the deoxygenated Hb with doubly higher precision as compared to oxygenated Hb, by setting the slide bar switch shown in FIG. 13 at a scale of about 6.7 (about two thirds position from the left side), the ratio of intensities of irradiated position is adjusted so that the ratio of measurement precision for oxygenated Hb against measurement precision for deoxygenated Hb is about 1:2 (Refer t thin lines in FIGS. 9 and 10).

In the case shown in FIG. 12, even when a plurality of measurement objects are selected, measurement errors for all of the plurality of measurement objects can be minimized without showing the screen as shown in FIG. 13. For instance, it is assumed in the following description that oxygenated Hb and deoxygenated Hb in a living body are measured by using light in a first wavelength range having a peak wavelength at 782 nm and light in a second wavelength range having a peak wavelength at 830 nm. When a ratio of intensity of the light in the first wavelength range against that of the light in the second wavelength range is set to about 0.5:1.5, a measurement error for the oxygenated Hb is minimized, and when the ratio is set to about 1.2:0.8, a measurement error for the deoxygenated Hb is minimized. Therefore, for measurement of the two types of Hb with maximum precision, the ratio intensity of the light in the first wavelength range against that of the light in the second wavelength range must be set in two ways, i.e., to about 0.5:1.5 and about 1.2:0.8.

During one trial operation (for inducing cerebral activities in a trial subject for measurement of cerebral functions), by switching the two values of irradiated light intensities from time to time, the measurement errors for the two types of Hb can substantially be minimized. For instance, by switching between the two ratios of irradiated light intensities once per second, or by switching between the two ratios of irradiated light intensities once in each random period, the two types of hemoglobin can be measured with the minimum measurement errors.

The timing for switching may be selected to satisfy the needs for inducing cerebral activities. For instance, when a measurement session continuing for 10 seconds is repeated 10 times, by switching the ratio of two irradiated light intensities once in every session, cerebral activities can be measured 5 times with either one of the two ratios of irradiated light intensities.

In this embodiment, frequency-modulated continuous light is used as irradiated light, but also when pulsed light is used, the method in which a ratio of irradiated light intensities is switched is effective. In a case of pulsed light, also a method may be employed in which a ratio of irradiated light intensities is switched for each pulse.

By switching between a plurality of ratios of irradiated light intensities, the sampling time space becomes longer, so that the time resolution becomes lower, but this reduction can be compensated to some extent by averaging results of several trials.

In this method, it is important to set the timing for switching a ratio of irradiated light intensities to prevent only a ratio of irradiated light intensities from being always used when stimulation is started. That is, it is required to acquire data using the two ratios of irradiated light intensities at any timing. By setting the timing for presenting stimulation and the timing for switching a ratio of irradiated light intensities so that the timings are reversed once in each trial, it is possible to efficiently and effectively average results of several trials.

Figure 14:
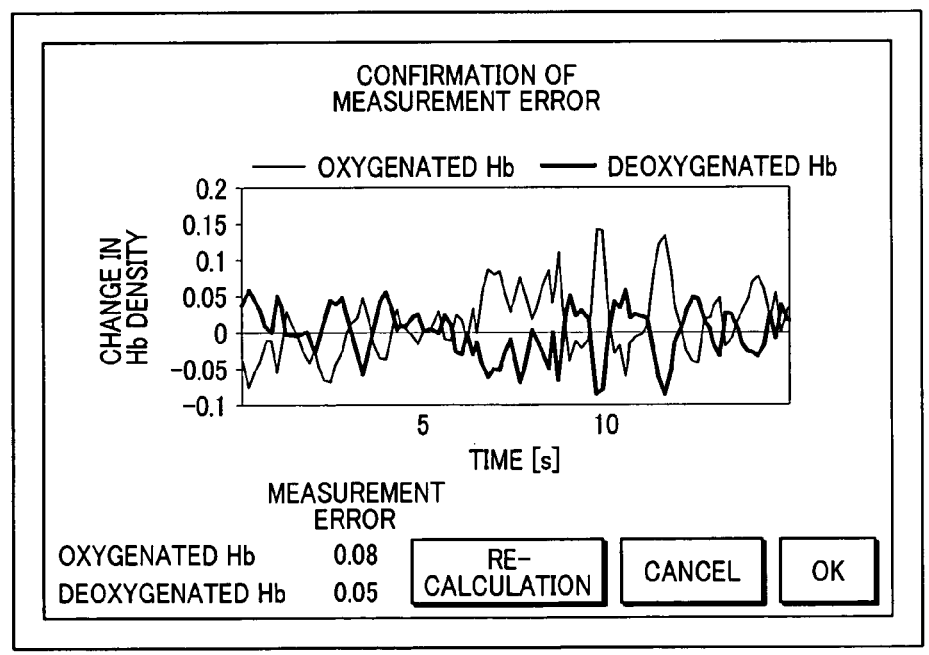
FIG. 14 illustrates an example of an operation screen used for selection of the next processing, showing a graph illustrating changes in densities of oxygenated Hb and deoxygenated Hb during measurement and measurement errors for the two types of Hb.
Figure 15:
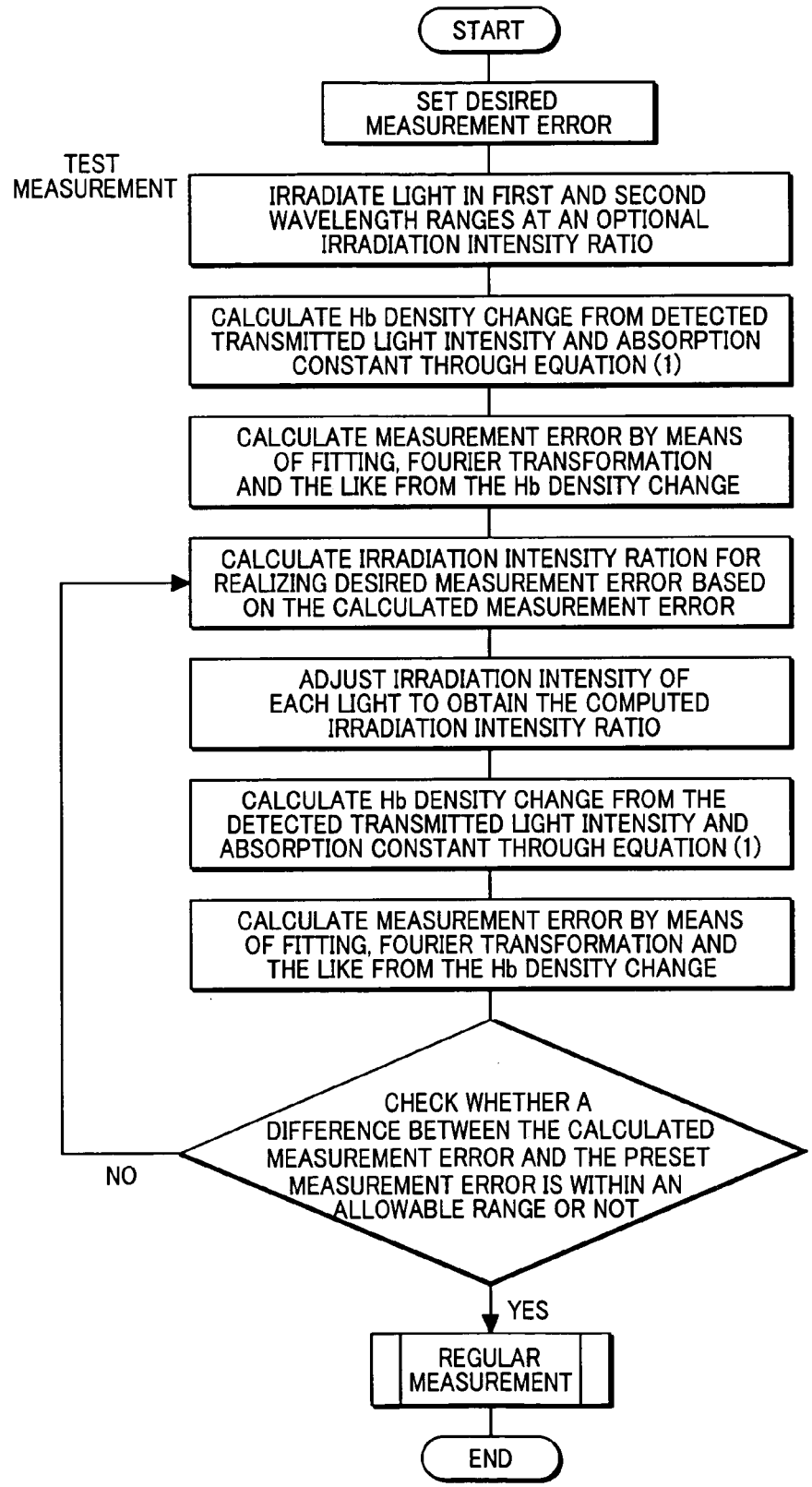
FIG. 15 is an example of a flow chart illustrating from setting of a desired measurement error to the start of the practical measurement.

Furthermore, after a ratio of irradiated light intensities required to realize a desired measurement error and intensity of irradiated light is adjusted, values of measurement errors generated in practical measurements can be displayed with a graph or with numerical values (refer to FIG. 14). A person responsible for measurement can select any of resetting (with the Cancel button), recalculation of measurement errors (with the Recalculation button) and continuation of measurement (with the OK button) by visually checking the waveform or the numerical values.

After a desired measurement error is determined, intensity of irradiated light in each wavelength range is adjusted so that a ratio of irradiated light intensities corresponding to the set condition described above is obtained, and then the practical measurement can be started.

With the present invention, a measurement error included in information from a living body can be reduced as compared to the conventional technology by changing a ratio of intensities of irradiated light in a plurality of wavelength ranges different in peak wavelength from each other.

What is claimed is:

1. Biological photometric equipment comprising:
    a light irradiating unit for irradiating a trial subject with mixed light obtained by mixing light in a first wavelength range having a peak wavelength at a first wavelength and light in a second wavelength range having a peak wavelength at a wavelength longer than the first wavelength; and
    a light receiving unit, adapted to be disposed on said trial subject, for detecting transmitted light irradiated from said light irradiating unit and propagating into the inside of said trial subject;
    wherein a value of said first wavelength is in the range from 650 nm to 800 nm and a value of said second wavelength is in the range from 810 nm to 900 nm;
    wherein a unit for changing a ratio of irradiated light intensities for measuring biological information concerning density of a light-absorbing material or changes in the densities in said trial subject is measured based on transmitted signals detected by said light receiving unit;
    wherein the unit for changing a ratio of irradiated light intensities maintains a sum of intensity of the irradiated light in said first wavelength range at a region X on the trial subject irradiated with the light and intensity of the irradiated light in said second wavelength range is kept not higher than a prespecified value; and
    wherein said intensity of irradiated light in said first wavelength range at said region X is at least either in the range from 0.3 to 0.7 times or in the range from 1.3 to 19 times as compared to that of irradiated light in said, second wavelength range.

2. The biological photometric equipment according to claim 1, wherein said unit for changing the ratio of irradiated light intensities changes said ratio so that the intensity of irradiated light in said first wavelength range at said region X is at least either in the range from 0.3 to 0.7 times or in the range from 1.3 to 10 times as compared to that of irradiated light in said second wavelength range when a value of said first wavelength is in the range from 700 nm to 790 nm.

3. The biological photometric equipment according to claim 1 further comprising:
    a unit for calculating a measurement error included in the biological information;
    a unit for calculating the ratio of irradiated light intensities required for setting the measurement error included in information obtained from the measured living body; and
    a unit for adjusting the irradiated light intensities based on a result of said calculations.

4. The biological photometric equipment according to claim 1 further comprising:
    a unit for switching the ratio of irradiated light intensities from time to time between "a" and "b", wherein "a" denotes a ratio of irradiated light in the first wavelength range against irradiated light in the second wavelength range at said region X substantially minimizing a measurement error included in a first information obtained from the measured trial subject, and "b" denotes a ratio of irradiated light in the first wavelength range against irradiated light in the second wavelength range at said region X substantially minimizing a measurement error included in a second information obtained from the measured trial subject.

5. The biological photometric equipment according to claim 4, wherein the first information obtained from the measured trial subject relates to density or changes in density of oxygenated hemoglobin, and the second information obtained from the measured trial subject relates to density or changes in density of deoxygenated hemoglobin.

6. The biological, photometric equipment according to claim 1 further comprising an anchoring tool holding a plurality of said light irradiating units and said light receiving units and configured to be set on a head portion of the trial subject, wherein said anchoring tool has said plurality of holes provided thereon for setting therein optical fibers for said plurality of light irradiating units and a plurality of light receiving units alternately provided in lattice form.

* * * * *